(12) United States Patent
Clark et al.

(10) Patent No.: US 11,413,047 B2
(45) Date of Patent: *Aug. 16, 2022

(54) OCCLUSIVE MEDICAL IMPLANT

(71) Applicant: BOSTON SCIENTIFIC SCIMED INC., Maple Grove, MN (US)

(72) Inventors: Christopher J. Clark, St. Michael, MN (US); Mark McPhail, Maple Grove, MN (US); Brian J. Tischler, Shoreview, MN (US); Dennis A. Peiffer, Brooklyn Park, MN (US); Burns P. Doran, Monticello, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 279 days.

This patent is subject to a terminal disclaimer.

(21) Appl. No.: 16/597,232

(22) Filed: Oct. 9, 2019

(65) Prior Publication Data

US 2020/0038033 A1 Feb. 6, 2020

Related U.S. Application Data

(63) Continuation of application No. 15/647,523, filed on Jul. 12, 2017, now Pat. No. 10,463,377, which is a (Continued)

(51) Int. Cl.
*A61B 17/12* (2006.01)
*A61B 17/00* (2006.01)

(52) U.S. Cl.
CPC .... *A61B 17/12122* (2013.01); *A61B 17/0057* (2013.01); *A61B 17/12172* (2013.01);
(Continued)

(58) Field of Classification Search
CPC ... A61B 17/00; A61B 17/12; A61B 17/12022; A61B 17/12145; A61B 17/12122;
(Continued)

(56) References Cited

U.S. PATENT DOCUMENTS 178,283 A 6/1876 French
1,967,318 A 7/1934 Monahan
(Continued)

FOREIGN PATENT DOCUMENTS

DE 102010044746 A1 3/2012
EP 2074953 A1 1/2009
(Continued)

OTHER PUBLICATIONS

Cragg et al., "A New Percutaneous Vena Cava Filter," American journal of Radiology, 141: 601-604, Sep. 1983.
(Continued)

*Primary Examiner* — Vi X Nguyen
(74) *Attorney, Agent, or Firm* — Seager, Tufte & Wickhem LLP

(57) ABSTRACT

An occlusive medical implant having a frame actuatable between a collapsed delivery configuration and an expanded implanted configuration, the frame including a generally tubular portion with a threaded insert configured to removably attach to a threaded distal end of a core wire; an occlusive element disposed on the frame; where a proximal portion of the occlusive element and the proximalmost extent of the threaded insert are substantially coplanar with a plane defined by three or more proximalmost extents of the frame in the expanded implanted configuration.

11 Claims, 15 Drawing Sheets

Related U.S. Application Data continuation of application No. 14/586,707, filed on Dec. 30, 2014, now Pat. No. 9,730,701.

(60) Provisional application No. 61/928,260, filed on Jan. 16, 2014.

(52) U.S. Cl.
CPC .............. *A61B 2017/00575* (2013.01); *A61B 2017/00579* (2013.01); *A61B 2017/00592* (2013.01); *A61B 2017/00597* (2013.01); *A61B 2017/00623* (2013.01); *A61B 2017/1205* (2013.01); *A61B 2017/12095* (2013.01)

(58) Field of Classification Search
CPC .......... A61B 17/0057; A61B 17/12172; A61B 2017/1205
See application file for complete search history.

(56) References Cited

U.S. PATENT DOCUMENTS

| | | |
|---|---|---|
| 3,844,302 A | 10/1974 | Klein |
| 3,874,388 A | 4/1975 | King et al. |
| 4,007,743 A | 2/1977 | Blake |
| 4,108,420 A | 8/1978 | West et al. |
| 4,341,218 A | 7/1982 | Ü |
| 4,585,000 A | 4/1986 | Hershenson |
| 4,603,693 A | 8/1986 | Conta et al. |
| 4,665,906 A | 5/1987 | Jervis |
| 4,710,192 A | 12/1987 | Liotta et al. |
| 4,832,055 A | 5/1989 | Palestrant |
| 4,873,978 A | 10/1989 | Ginsburg |
| 4,917,089 A | 4/1990 | Sideris |
| 4,921,484 A | 5/1990 | Hillstead |
| 5,037,810 A | 8/1991 | Saliba |
| 5,041,090 A | 8/1991 | Scheglov et al. |
| 5,041,093 A | 8/1991 | Chu |
| 5,042,707 A | 8/1991 | Taheri |
| 5,053,009 A | 10/1991 | Herzberg |
| 5,064,435 A | 11/1991 | Porter |
| 5,078,736 A | 1/1992 | Behl |
| 5,171,259 A | 12/1992 | Inoue |
| 5,171,383 A | 12/1992 | Sagae et al. |
| 5,176,692 A | 1/1993 | Wilk et al. |
| 5,192,301 A | 3/1993 | Kamiya et al. |
| 5,256,146 A | 10/1993 | Ensminger et al. |
| 5,258,000 A | 11/1993 | Gianturco |
| 5,258,042 A | 11/1993 | Mehta |
| 5,284,488 A | 2/1994 | Sideris |
| 5,306,234 A | 4/1994 | Johnson |
| 5,334,217 A | 8/1994 | Das |
| 5,350,399 A | 9/1994 | Erlebacher et al. |
| 5,353,784 A | 10/1994 | Nady-Mohamed |
| 5,370,657 A | 12/1994 | Irie |
| 5,375,612 A * | 12/1994 | Cottenceau ........... A61F 2/0105 128/899 |
| 5,417,699 A | 5/1995 | Klein et al. |
| 5,421,832 A | 6/1995 | Lefebvre |
| 5,425,744 A | 6/1995 | Fagan et al. |
| 5,433,727 A | 7/1995 | Sideris |
| 5,443,454 A | 8/1995 | Tanabe et al. |
| 5,451,235 A | 9/1995 | Lock et al. |
| 5,464,408 A | 11/1995 | Duc |
| 5,469,867 A | 11/1995 | Schmitt |
| 5,490,856 A | 2/1996 | Person et al. |
| 5,522,822 A | 6/1996 | Phelps et al. |
| 5,522,836 A | 6/1996 | Palermo |
| 5,527,322 A | 6/1996 | Klein et al. |
| 5,527,338 A | 6/1996 | Purdy |
| 5,591,196 A | 1/1997 | Marin et al. |
| 5,614,204 A | 3/1997 | Cochrum |
| 5,634,936 A | 6/1997 | Linden et al. |
| 5,634,942 A | 6/1997 | Chevillon et al. |
| 5,637,097 A | 6/1997 | Yoon |
| 5,643,292 A | 7/1997 | Hart |
| 5,649,953 A | 7/1997 | Lefebvre |
| 5,662,671 A | 9/1997 | Barbut et al. |
| 5,669,933 A | 9/1997 | Simon et al. |
| 5,693,067 A | 12/1997 | Purdy |
| 5,695,525 A | 12/1997 | Mulhauser et al. |
| 5,702,421 A | 12/1997 | Schneidt |
| 5,709,224 A | 1/1998 | Behl et al. |
| 5,709,707 A | 1/1998 | Lock et al. |
| 5,725,552 A | 3/1998 | Kotula et al. |
| 5,725,568 A | 3/1998 | Hastings |
| 5,733,294 A | 3/1998 | Forber et al. |
| 5,735,290 A | 4/1998 | Sterman et al. |
| 5,749,883 A | 5/1998 | Halpern |
| 5,749,894 A | 5/1998 | Engelson |
| 5,766,219 A | 6/1998 | Horton |
| 5,766,246 A | 6/1998 | Mulhauser et al. |
| 5,769,816 A | 6/1998 | Barbut et al. |
| 5,776,097 A | 7/1998 | Massoud |
| 5,776,162 A | 7/1998 | Kleshinski |
| 5,782,860 A | 7/1998 | Epstein et al. |
| 5,810,874 A | 9/1998 | Lefebvre |
| 5,823,198 A | 10/1998 | Jones et al. |
| 5,830,228 A | 11/1998 | Knapp et al. |
| 5,836,913 A | 11/1998 | Orth et al. |
| 5,836,968 A | 11/1998 | Simon et al. |
| 5,846,260 A | 12/1998 | Maahs |
| 5,846,261 A | 12/1998 | Kotula et al. |
| 5,849,005 A | 12/1998 | Garrison et al. |
| 5,851,232 A | 12/1998 | Lois |
| 5,855,597 A | 1/1999 | Jayaraman |
| 5,865,791 A | 2/1999 | Whayne et al. |
| 5,865,802 A | 2/1999 | Yoon et al. |
| 5,868,702 A | 2/1999 | Stevens et al. |
| 5,868,708 A | 2/1999 | Hart et al. |
| 5,876,367 A | 3/1999 | Kaganov et al. |
| 5,882,340 A | 3/1999 | Yoon |
| 5,885,258 A | 3/1999 | Sachdeva et al. |
| 5,895,399 A | 4/1999 | Barbut et al. |
| 5,902,289 A | 5/1999 | Swartz et al. |
| 5,904,703 A | 5/1999 | Gilson |
| 5,906,207 A | 5/1999 | Shen |
| 5,910,154 A | 6/1999 | Tsugita et al. |
| 5,911,734 A | 6/1999 | Tsugita et al. |
| 5,916,236 A | 6/1999 | Muijs Van de Moer et al. |
| 5,928,192 A | 7/1999 | Maahs |
| 5,928,260 A | 7/1999 | Chin et al. |
| 5,931,818 A | 8/1999 | Werp et al. |
| 5,935,147 A | 8/1999 | Kensey et al. |
| 5,935,148 A | 8/1999 | Villar et al. |
| 5,941,249 A | 8/1999 | Maynard |
| 5,944,738 A | 8/1999 | Amplatz et al. |
| 5,947,997 A | 9/1999 | Pavcnik et al. |
| 5,951,589 A | 9/1999 | Epstein et al. |
| 5,954,694 A | 9/1999 | Sunseri |
| 5,954,767 A | 9/1999 | Pajotin et al. |
| 5,957,940 A | 9/1999 | Tanner et al. |
| 5,976,174 A | 11/1999 | Ruiz |
| 5,980,514 A | 11/1999 | Kupiecki et al. |
| 5,980,555 A | 11/1999 | Barbut et al. |
| 5,989,281 A | 11/1999 | Barbut et al. |
| 5,993,469 A | 11/1999 | McKenzie et al. |
| 5,997,557 A | 12/1999 | Barbut et al. |
| 6,007,523 A | 12/1999 | Mangosong |
| 6,007,557 A | 12/1999 | Ambrisco et al. |
| 6,010,517 A | 1/2000 | Baccaro |
| 6,010,522 A | 1/2000 | Barbut et al. |
| 6,024,754 A | 2/2000 | Engelson |
| 6,024,755 A | 2/2000 | Addis |
| 6,024,756 A | 2/2000 | Huebsch et al. |
| 6,027,520 A | 2/2000 | Tsugita et al. |
| 6,033,420 A | 3/2000 | Hahnen |
| 6,042,598 A | 3/2000 | Tsugita et al. |
| 6,048,331 A | 4/2000 | Tsugita et al. |
| 6,051,014 A | 4/2000 | Jang |
| 6,051,015 A | 4/2000 | Maahs |
| 6,056,720 A | 5/2000 | Morse |
| 6,068,621 A | 5/2000 | Balceta et al. |
| 6,074,357 A | 6/2000 | Kaganov et al. |

(56) References Cited

U.S. PATENT DOCUMENTS

| | | |
|---|---|---|
| 6,079,414 A | 6/2000 | Roth |
| 6,080,182 A | 6/2000 | Shaw et al. |
| 6,080,183 A | 6/2000 | Tsugita et al. |
| 6,083,239 A | 7/2000 | Addis |
| 6,132,438 A | 10/2000 | Fleischman et al. |
| 6,136,016 A | 10/2000 | Barbut et al. |
| 6,139,527 A | 10/2000 | Laufer et al. |
| 6,152,144 A | 11/2000 | Lesh et al. |
| 6,159,195 A | 12/2000 | Ha et al. |
| 6,161,543 A | 12/2000 | Cox et al. |
| 6,168,615 B1 | 1/2001 | Ken et al. |
| 6,193,739 B1 | 2/2001 | Chevillon et al. |
| 6,203,531 B1 | 3/2001 | Ockuly et al. |
| 6,231,561 B1 | 5/2001 | Frazier et al. |
| 6,231,589 B1 | 5/2001 | Wessman et al. |
| 6,267,772 B1 | 7/2001 | Mulhauser et al. |
| 6,328,755 B1 | 12/2001 | Marshall |
| 6,402,771 B1 | 6/2002 | Palmer et al. |
| 6,458,145 B1 | 10/2002 | Ravenscroft et al. |
| 6,464,712 B1 | 10/2002 | Epstein et al. |
| 6,485,501 B1 | 11/2002 | Green |
| 6,533,782 B2 | 3/2003 | Howell et al. |
| 6,569,184 B2 | 5/2003 | Huter |
| 6,589,214 B2 | 7/2003 | McGuckin et al. |
| 6,599,308 B2 | 7/2003 | Amplatz |
| 6,602,271 B2 | 8/2003 | Adams et al. |
| 6,641,564 B1 | 11/2003 | Kraus |
| 6,650,923 B1 | 11/2003 | Lesh et al. |
| 6,689,150 B1 | 2/2004 | VanTassel et al. |
| 6,712,836 B1 | 3/2004 | Berg et al. |
| 6,755,812 B2 | 6/2004 | Peterson et al. |
| 7,037,321 B2 | 5/2006 | Sachdeva et al. |
| 7,044,134 B2 | 5/2006 | Khairkhahan et al. |
| 7,097,651 B2 | 8/2006 | Harrison et al. |
| 7,179,275 B2 | 2/2007 | McGuckin et al. |
| 7,226,466 B2 | 6/2007 | Opolski |
| 7,303,526 B2 | 12/2007 | Sharkey et al. |
| 7,323,002 B2 | 1/2008 | Johnson et al. |
| 7,678,123 B2 | 3/2010 | Chanduszko |
| 7,695,425 B2 | 4/2010 | Schweich et al. |
| 7,780,694 B2 | 8/2010 | Palmer et al. |
| 7,811,314 B2 | 10/2010 | Fierens et al. |
| 7,927,365 B2 | 4/2011 | Fierens et al. |
| 7,972,359 B2 | 7/2011 | Kreidler |
| 9,730,701 B2 | 8/2017 | Tischler et al. |
| 2003/0181942 A1 | 9/2003 | Sutton et al. |
| 2003/0220667 A1 | 11/2003 | Van Der Burg et al. |
| 2004/0044361 A1 | 3/2004 | Frazier et al. |
| 2007/0066993 A1 | 3/2007 | Kreidler |
| 2007/0162048 A1 | 7/2007 | Quinn et al. |
| 2009/0062841 A1 | 3/2009 | Amplatz et al. |
| 2009/0099647 A1 | 4/2009 | Glimsdale et al. |
| 2011/0054515 A1 | 3/2011 | Bridgeman et al. |
| 2011/0301630 A1 | 12/2011 | Hendriksen et al. |
| 2012/0172927 A1 | 7/2012 | Campbell et al. |
| 2012/0239083 A1 | 9/2012 | Kreidler |
| 2013/0138138 A1* | 5/2013 | Clark ............... A61B 17/12022 606/200 |
| 2013/0211492 A1 | 8/2013 | Schneider et al. |

FOREIGN PATENT DOCUMENTS

| | | |
|---|---|---|
| JP | 2012501793 A | 1/2012 |
| WO | 9313712 A1 | 7/1993 |
| WO | 9721402 A1 | 6/1997 |
| WO | 9726939 A1 | 7/1997 |
| WO | 9728749 A1 | 8/1997 |
| WO | 9802100 A1 | 1/1998 |
| WO | 9817187 A1 | 4/1998 |
| WO | 9823322 A1 | 6/1998 |
| WO | 9907289 A1 | 2/1999 |
| WO | 9908607 A1 | 2/1999 |
| WO | 9930640 A1 | 6/1999 |
| WO | 9959479 A1 | 11/1999 |
| WO | 0001308 A1 | 1/2000 |
| WO | 0027292 A1 | 5/2000 |
| WO | 0053120 A1 | 9/2000 |
| WO | 0121247 A1 | 3/2001 |
| WO | 0126726 A1 | 4/2001 |
| WO | 0130266 A1 | 5/2001 |
| WO | 2013060855 A1 | 5/2013 |
| WO | 2014011865 A1 | 1/2014 |

OTHER PUBLICATIONS

Cragg et al., "Nonsurgical Placement of Arterial Endoprostheses: A New ATechnique Using Nitinol Wire," Radiology, 147(1): 261-263, Apr. 1983.

Lock et al., "Transcatheter Closure of Atrial Septal Defects," Circulation, 79(5): 1091-1099, May 1989.

Lock et al., "Transcatheter Umbrella Closure of Congenital Heart Defects," Circulation, 75(3): 593-599, Mar. 1987.

Rashkind et al., "Nonsurgical Closure of Patent Ductus Arteriosus: Clinical Application of the Rashking PDA Occluder System," Circulation, 75(3): 583-592, Mar. 1987.

Rosengart et al., "Percutaneous and Minimally Invasive Valve Procedures," Circulation, 117: 1750-1767, Apr. 1, 2008.

Ruttenberg, "Nonsurgical Therapy of Cardiac Disorders," Pediatric Consult, 5(2), 1986.

Sugita et al., "Nonsurgical Implanatations of a Vascular Ring Prothesis Using Thermal Shape Memory Ti/Ni Alloy (Nitinol Wire)," Trans. Am. Soc. Artif. Intern. Organs., XXXII: 30-34, 1986.

Wessel et al., "Outpatient Closure of the Patent Ductus Arteriousus," Circulation, 77(5): 1068-1071, 1988.

Tung et al., U.S. Appl. No. 61/559,941, filed Nov. 15, 2011.

Yue Yu et al., U.S. Appl. No. 61/557,880, filed Dec. 20, 2011.

\* cited by examiner

OCCLUSIVE MEDICAL IMPLANT

CROSS-REFERENCE TO RELATED APPLICATIONS

This application is a continuation of U.S. application Ser. No. 15/647,523, filed Jul. 12, 2017, which is a continuation of U.S. application Ser. No. 14/586,707 filed Dec. 30, 2014, now U.S. Pat. No. 9,730,701, which claims priority benefit to U.S. Provisional Application Ser. No. 61/928,260 filed Jan. 16, 2014.

TECHNICAL FIELD

The disclosure relates generally to percutaneous medical devices and more particularly to percutaneous medical devices for implantation into the left atrial appendage (LAA) of a heart.

BACKGROUND

Atrial fibrillation (AF) is the most common sustained cardiac arrhythmia, affecting over 5.5 million people worldwide. Atrial fibrillation is the irregular, chaotic beating of the upper chambers of the heart. Electrical impulses discharge so rapidly that the atrial muscle quivers, or fibrillates. Episodes of atrial fibrillation may last a few minutes or several days. The most serious consequence of atrial fibrillation is ischemic stroke. It has been estimated that up to 20% of all strokes are related to atrial fibrillation. Most atrial fibrillation patients, regardless of the severity of their symptoms or frequency of episodes, require treatment to reduce the risk of stroke. The left atrial appendage (LAA) is a small organ attached to the left atrium of the heart as a pouch-like extension. In patients suffering from atrial fibrillation, the left atrial appendage may not properly contract with the left atrium, causing stagnant blood to pool within its interior, which can lead to the undesirable formation of thrombi within the left atrial appendage. Thrombi forming in the left atrial appendage may break loose from this area and enter the blood stream. Thrombi that migrate through the blood vessels may eventually plug a smaller vessel downstream and thereby contribute to stroke or heart attack. Clinical studies have shown that the majority of blood clots in patients with atrial fibrillation are found in the left atrial appendage. As a treatment, medical devices have been developed which are positioned in the left atrial appendage and deployed to close off the ostium of the left atrial appendage. Over time, the exposed surface(s) spanning the ostium of the left atrial appendage becomes covered with tissue (a process called endothelization), effectively removing the left atrial appendage from the circulatory system and reducing or eliminating the amount of thrombi which may enter the blood stream from the left atrial appendage.

A continuing need exists for improved medical devices and methods to control thrombus formation within the left atrial appendage of patients suffering from atrial fibrillation.

SUMMARY

A medical implant may include a frame configured to actuate between a collapsed configuration and an expanded configuration, and an occlusive element covering at least a portion of the frame, wherein a proximal end of the frame forms a generally tubular portion, the tubular portion being configured to attach to a distal end of a core wire, and wherein the tubular portion of the frame includes a threaded insert coupled thereto.

An occlusive implant system may include a catheter having a lumen extending therethrough, a core wire slidably and rotatably disposed within the lumen, the core wire having a threaded member disposed at a distal end thereof, and a medical implant having an expandable frame, an occlusive element disposed on the frame, and a threaded insert coupled to a proximal portion of the frame, wherein the threaded member is removably coupled to the threaded insert.

A method of making a centering core wire may include obtaining an elongate core wire having a threaded member disposed at a distal end thereof; obtaining a guide element having an aperture or lumen disposed therein; inserting a proximal end of the elongate core wire into the aperture or lumen; sliding the guide element distally over the elongate core wire into contact with the threaded member; and applying a polymeric jacket over the elongate core wire from the proximal end to the guide element; wherein the polymeric jacket retains the guide element against the threaded member.

Figure 1:
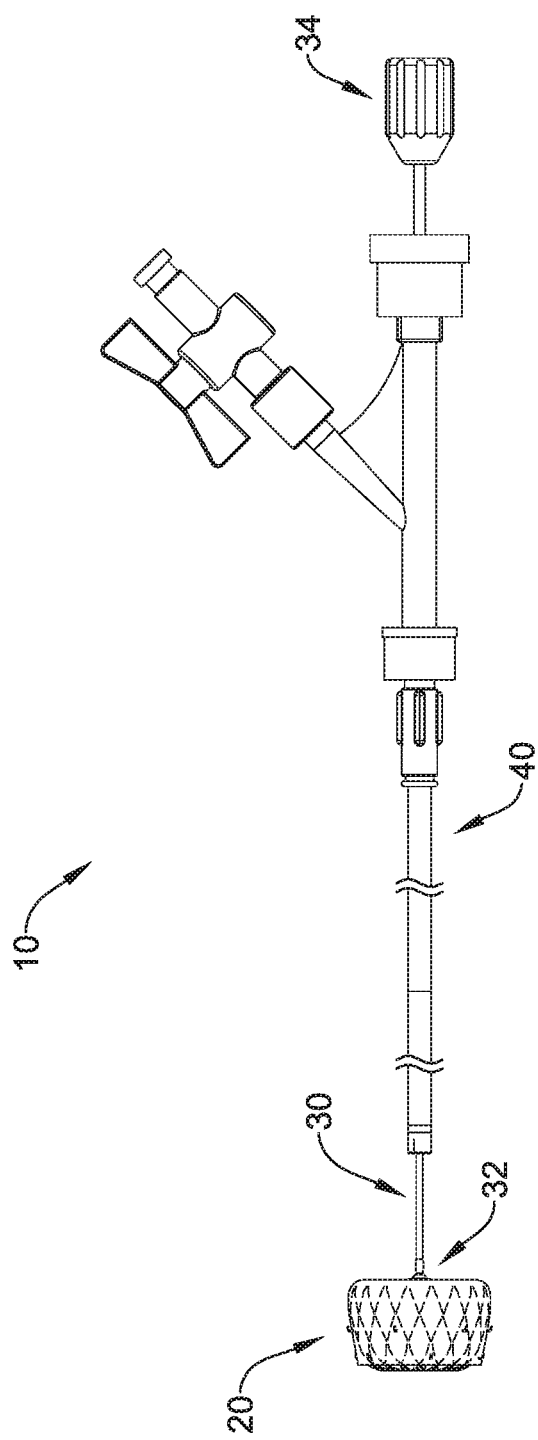
FIG. 1 is a side view of an example medical implant and delivery assembly.

While the invention is amenable to various modifications and alternative forms, specifics thereof have been shown by way of example in the drawings and will be described in greater detail below. It should be understood, however, that the intention is not to limit the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

The terms "upstream" and "downstream" refer to a position or location relative to the direction of blood flow through a particular element or location, such as a vessel (i.e., the aorta), a heart valve (i.e., the aortic valve), and the like.

The terms "proximal" and "distal" shall generally refer to the relative position, orientation, or direction of an element or action, from the perspective of a clinician using the medical device, relative to one another. While the terms are not meant to be limiting, "proximal" may generally be considered closer to the clinician or an exterior of a patient, and "distal" may generally be considered to be farther away from the clinician, along the length of the medical device.

The terms "monolithic" and "unitary" shall generally refer to an element or elements made from or consisting of a single structure or base unit/element. A monolithic and/or unitary element shall exclude structure and/or features made by assembling or otherwise joining multiple discrete elements together.

All numeric values are herein assumed to be modified by the term "about," whether or not explicitly indicated. The term "about", in the context of numeric values, generally refers to a range of numbers that one of skill in the art would consider equivalent to the recited value (i.e., having the same function or result). In many instances, the term "about" may include numbers that are rounded to the nearest significant figure. Other uses of the term "about" (i.e., in a context other than numeric values) may be assumed to have their ordinary and customary definition(s), as understood from and consistent with the context of the specification, unless otherwise specified.

Weight percent, percent by weight, wt %, wt-%, % by weight, and the like are synonyms that refer to the concentration of a substance as the weight of that substance divided by the weight of the composition and multiplied by 100.

The recitation of numerical ranges by endpoints includes all numbers within that range, including the endpoints (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following description should be read with reference to the drawings wherein like reference numerals indicate like elements throughout the several views. The detailed description and drawings are intended to illustrate but not limit the claimed invention. Those skilled in the art will recognize that the various elements described and/or shown may be arranged in various combinations and configurations without departing from the scope of the disclosure. The various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

The occurrence of thrombi in the left atrial appendage (LAA) during atrial fibrillation may be due to stagnancy of the blood pool in the LAA. The blood may still be pulled out of the left atrium by the left ventricle, however less effectively due to the irregular contraction of the left atrium caused by atrial fibrillation. Therefore, instead of an active support of the blood flow by a contracting left atrium and left atrial appendage, filling of the left ventricle may depend primarily or solely on the suction effect created by the left ventricle. Further, the contraction of the left atrial appendage may not be in sync with the cycle of the left ventricle. For example, contraction of the left atrial appendage may be out of phase up to 180 degrees with the left ventricle, which may create significant resistance to the desired flow of blood. Further still, most left atrial appendage geometries are complex and highly variable, with large irregular surface areas and a narrow ostium or opening compared to the depth of the left atrial appendage. These aspects as well as others, taken individually or in various combinations, may lead to high flow resistance of blood out of the left atrial appendage.

In an effort to reduce the occurrence of thrombi formation within the left atrial appendage and prevent thrombi from entering the blood stream from within the left atrial appendage, medical devices have been developed that close off the left atrial appendage from the heart and/or circulatory system, thereby lowering the risk of stroke due to thrombolytic material entering the blood stream from the left atrial appendage. Difficulties encountered during placement of said medical device(s) may occasionally require removal and/or recapture procedures. In an effort to ease recapture procedures and/or to provide a medical device suitable for long term implantation, favorable new features have been developed.

Figure 2:
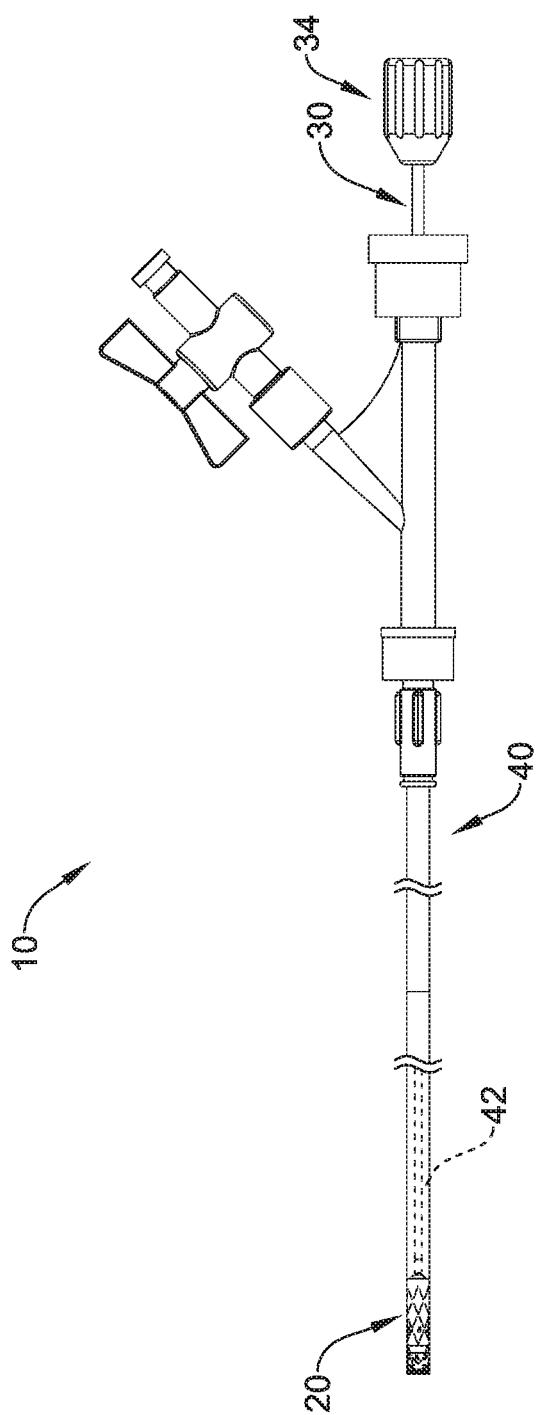
FIG. 2 is a partial cross-sectional view of an example medical implant disposed within a delivery assembly.

Turning now to the figures, FIG. 1 illustrates an example delivery assembly and/or implant system 10 including an example medical implant 20 disposed at a distal end 32 of an example core wire 30. The core wire 30 may be slidably and/or rotatably disposed within a lumen 42 of a delivery catheter 40. In some embodiments, a proximal end 34 of the core wire 30 may extend proximally of a proximal end of the delivery catheter 40 for manual manipulation by a clinician or practitioner. In some embodiments, the example medical implant 20 may be removably attached, joined, or otherwise connected to the distal end 32 of the example core wire 30. An example medical implant 20 may be configured to actuate from a collapsed configuration to an expanded configuration when (or after being) extended distally from the delivery catheter 40, as seen in FIG. 1 for example. FIG. 2 illustrates the example medical implant 20 disposed within a distal portion of the lumen 42 of the delivery catheter 40 in the collapsed configuration. It is contemplated that any and/or all example medical implants disclosed herein may be used in accordance with and/or be associated with the example delivery assembly and/or implant system 10 described above.

Figure 3:
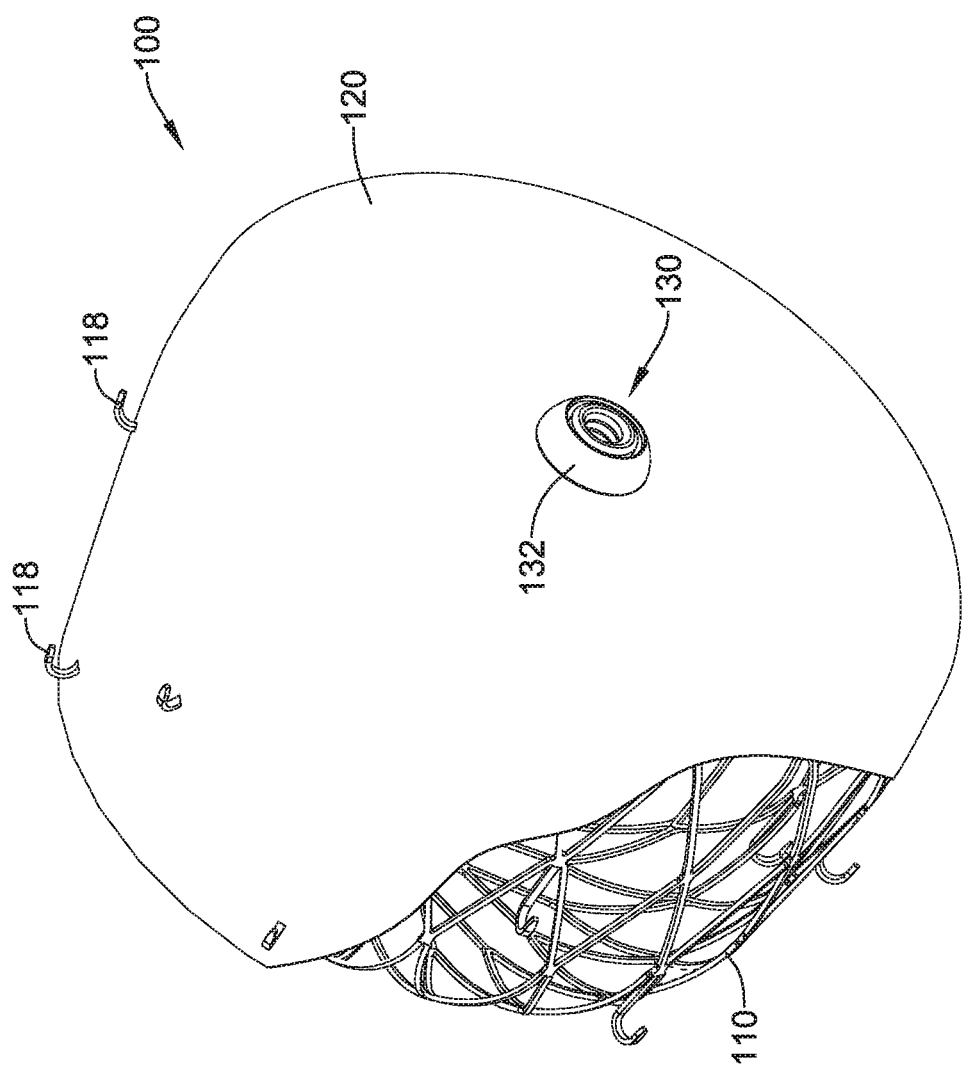
FIG. 3 is a perspective view of an example medical implant.
Figure 3A:
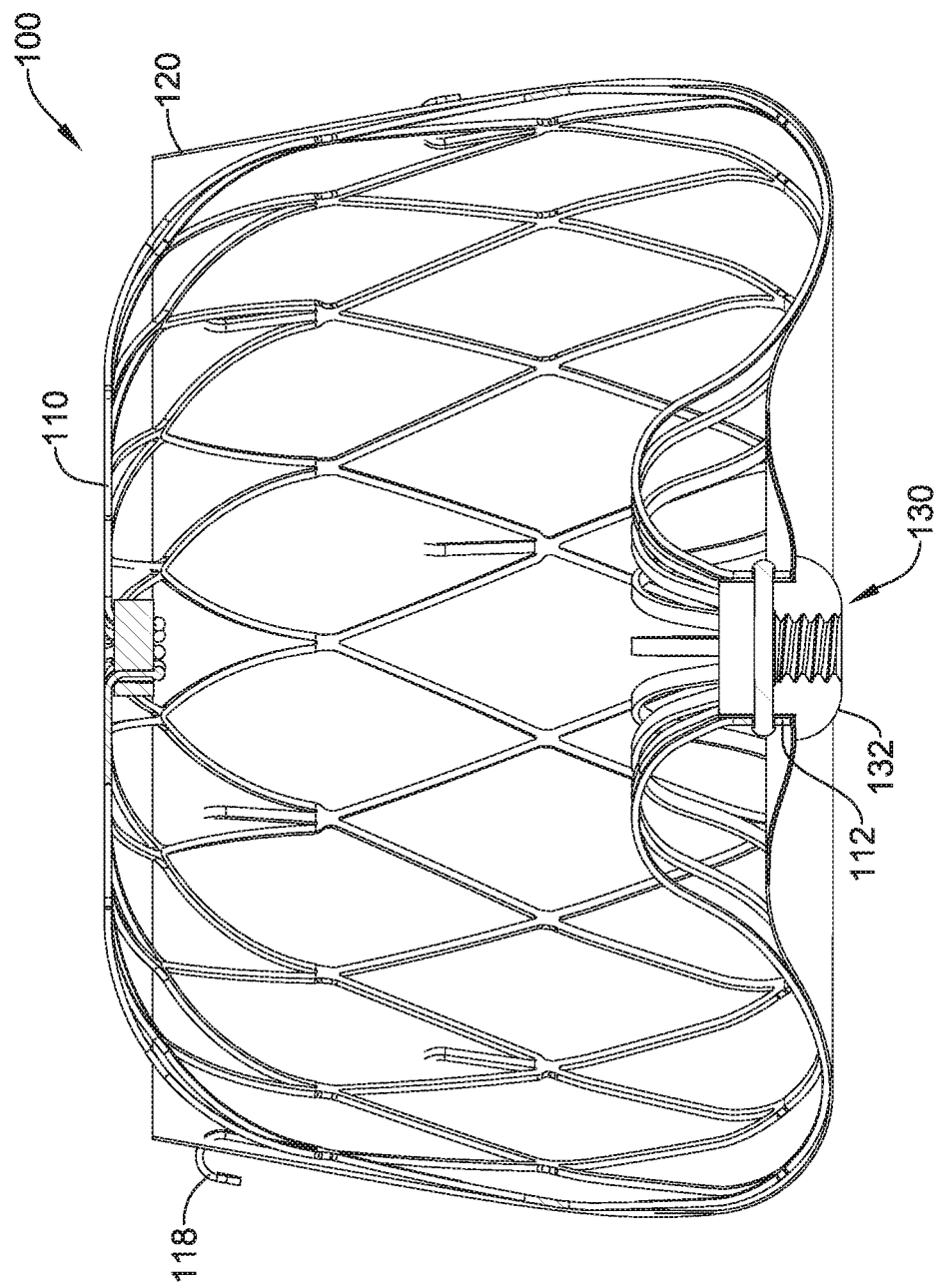
FIG. 3A is a partial cross-sectional view of the example medical implant of FIG. 3.

FIGS. 3 and 3A illustrate an example medical implant 100 having a frame 110 configured to actuate between a collapsed configuration and an expanded configuration. In some embodiments, the example medical implant 100 may include an occlusive element 120 disposed on, disposed over, disposed about, or covering at least a portion of the frame 110. In some embodiments, the occlusive element 120 may be disposed on, disposed over, disposed about or cover at least a portion of an outer (or outwardly-facing) surface of the frame 110. In some embodiments, a proximal end of the frame 110 may form a generally tubular portion 112, the generally tubular portion 112 being configured to attach to or couple to a distal end of a core wire 30. In some embodiments, the generally tubular portion 112 of the frame 110 may include a threaded insert 130 coupled thereto. In some embodiments, the threaded insert 130 may be at least partially disposed within the generally tubular portion 112 of the frame 110. In some embodiments, the threaded insert 130 may be configured to and/or adapted to couple with, join to, mate with, or otherwise engage a threaded member 36 disposed at the distal end 32 of the core wire 30.

In some embodiments, a first portion of the occlusive element 120 may be disposed between the threaded insert 130 and the generally tubular portion 112. In some embodiments, the first portion of the occlusive element 120 may be pinched or held between the threaded insert 130 and the generally tubular portion 112. In some embodiments, the threaded insert 130 may include a curved or angled proximally-facing surface 132 that extends radially outward from threads formed within a center of the threaded insert 130. In some embodiments, the curved or angled proximally-facing surface 132 may extend proximally of the occlusive element 120 in the expanded configuration and/or the collapsed configuration. In some embodiments, the curved or angled proximally-facing surface 132 may have an outer extent that is disposed radially outward from the first portion of the occlusive element 120 and/or the generally tubular portion 112. In some embodiments, the frame 110 may include a plurality of proximally-facing hooks 118 disposed about a periphery of the frame 110 in the expanded configuration. In some embodiments, the plurality of proximally-facing hooks 118 may provide an anchoring mechanism to aid in retaining a deployed medical implant 100 at a target site within a patient's anatomy (i.e., the left atrial appendage, for example).

Figure 4:
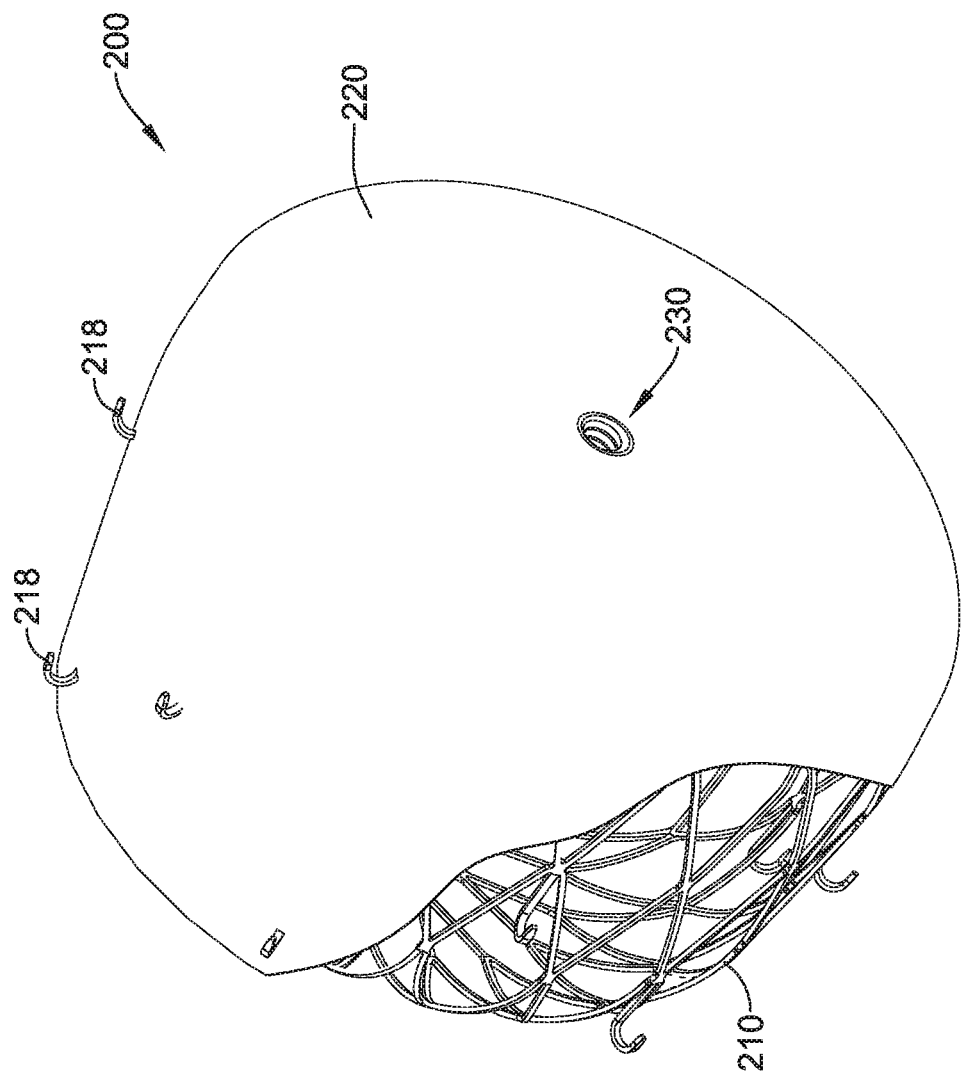
FIG. 4 is a perspective view of an example medical implant.
Figure 4A:
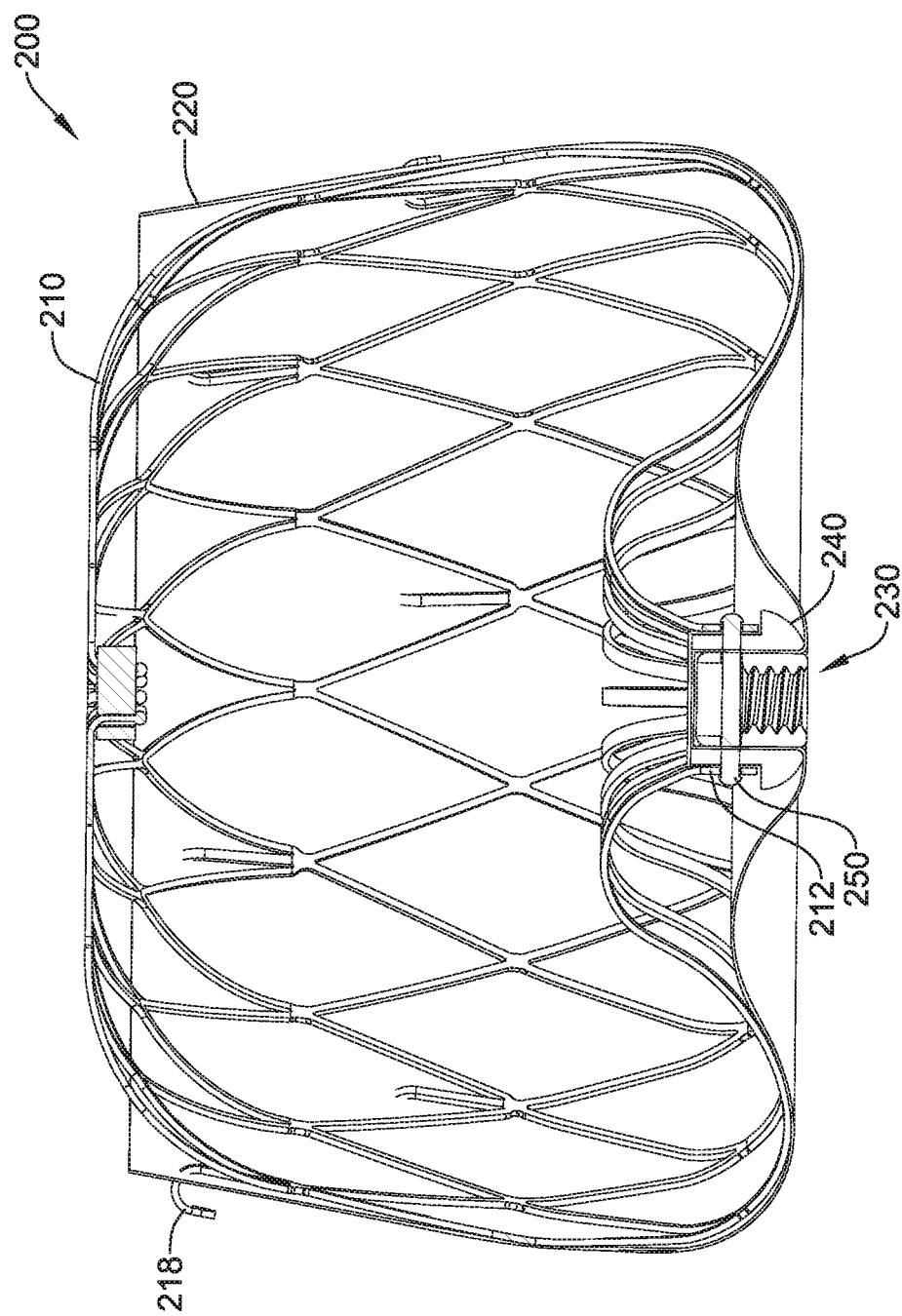
FIG. 4A is a partial cross-sectional view of the example medical implant of FIG. 4.

FIGS. 4 and 4A illustrate an example medical implant 200 having a frame 210 configured to actuate between a collapsed configuration and an expanded configuration. In some embodiments, the example medical implant 200 may include an occlusive element 220 disposed on, disposed over, disposed about, or covering at least a portion of the frame 210. In some embodiments, the occlusive element 220 may be disposed on, disposed over, disposed about or cover at least a portion of an outer (or outwardly-facing) surface of the frame 210. In some embodiments, a proximal end of the frame 210 may form a generally tubular portion 212, the generally tubular portion 212 being configured to attach to or couple to a distal end 32 of a core wire 30. In some embodiments, the generally tubular portion 212 of the frame 210 may include a threaded insert 230 coupled thereto. In some embodiments, the frame 210 may include an annular collar member 240 at least partially disposed within the generally tubular portion 212 and coupled thereto. In some embodiments, the threaded insert 230 may be coupled to the annular collar member 240. In some embodiments, the threaded insert 230 may be at least partially disposed within the annular collar member 240. In some embodiments, a pin element 250 may couple the annular collar member 240 and/or the threaded insert 230 to the frame 210 and/or to each other. In some embodiments, the annular collar member 240 and/or threaded insert 230 may be fixedly attached to and/or coupled with the generally tubular portion 212 of the frame 210 and/or each other. In some embodiments, the annular collar member 240 and/or threaded insert 230 may be permanently attached to and/or coupled with the generally tubular portion 212 of the frame 210 and/or each other. In some embodiments, the annular collar member 240 and/or threaded insert 230 may be removably attached to and/or coupled with the generally tubular portion 212 of the frame 210 and/or each other. In some embodiments, the threaded insert 230 may be configured to and/or adapted to reversibly and/or removably couple with, join to, mate with, or otherwise engage a threaded member 36 disposed at the distal end 32 of the core wire 30.

In some embodiments, a first portion of the occlusive element 220 may be disposed between the threaded insert 230 and the annular collar member 240. In some embodiments, the first portion of the occlusive element 220 may be pinched or held between the threaded insert 230 and the annular collar member 240. In some embodiments, the threaded insert 230 may be disposed distally of a portion of the occlusive element 220 disposed outside of the annular collar member 240 in the expanded configuration and/or the collapsed configuration. In some embodiments, an outer portion of the occlusive element 220 may be defined as that part of the occlusive element 220 disposed outside of the annular collar member 240. In some embodiments, the outer portion of the occlusive element 220 may be disposed radially outward from the threaded insert 230 in the expanded configuration. In some embodiments, the frame 210 may include a plurality of proximally-facing hooks 218 disposed about a periphery of the frame 210 in the expanded configuration. In some embodiments, the plurality of proximally-facing hooks 218 may provide an anchoring mechanism to aid in retaining a deployed medical implant 200 at a target site within a patient's anatomy (i.e., the left atrial appendage, for example).

In some embodiments, the medical implant 200 of FIG. 4 may have a reduced amount of exposed material (i.e., metallic material) at the threaded insert compared to the medical implant 100 of FIG. 3. Applicants have found that reducing the amount of metallic material exposed to the bloodstream may provide certain advantages such as reduced thrombus formation and/or more rapid endothelization.

Figure 5A:
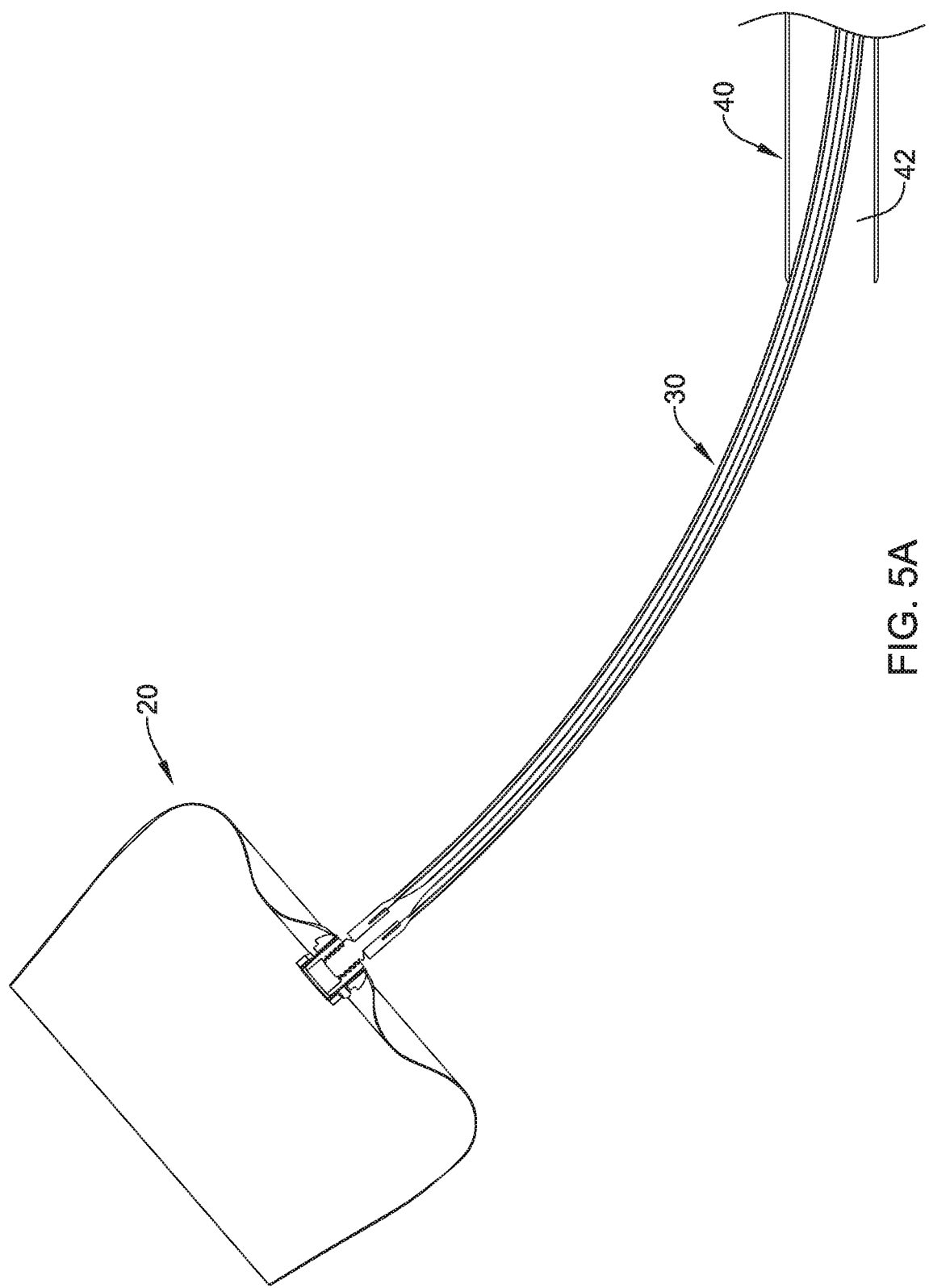
FIGS. 5A and 5B illustrate the extent of relative movement between certain elements of the delivery assembly of FIG. 1.
Figure 5B:
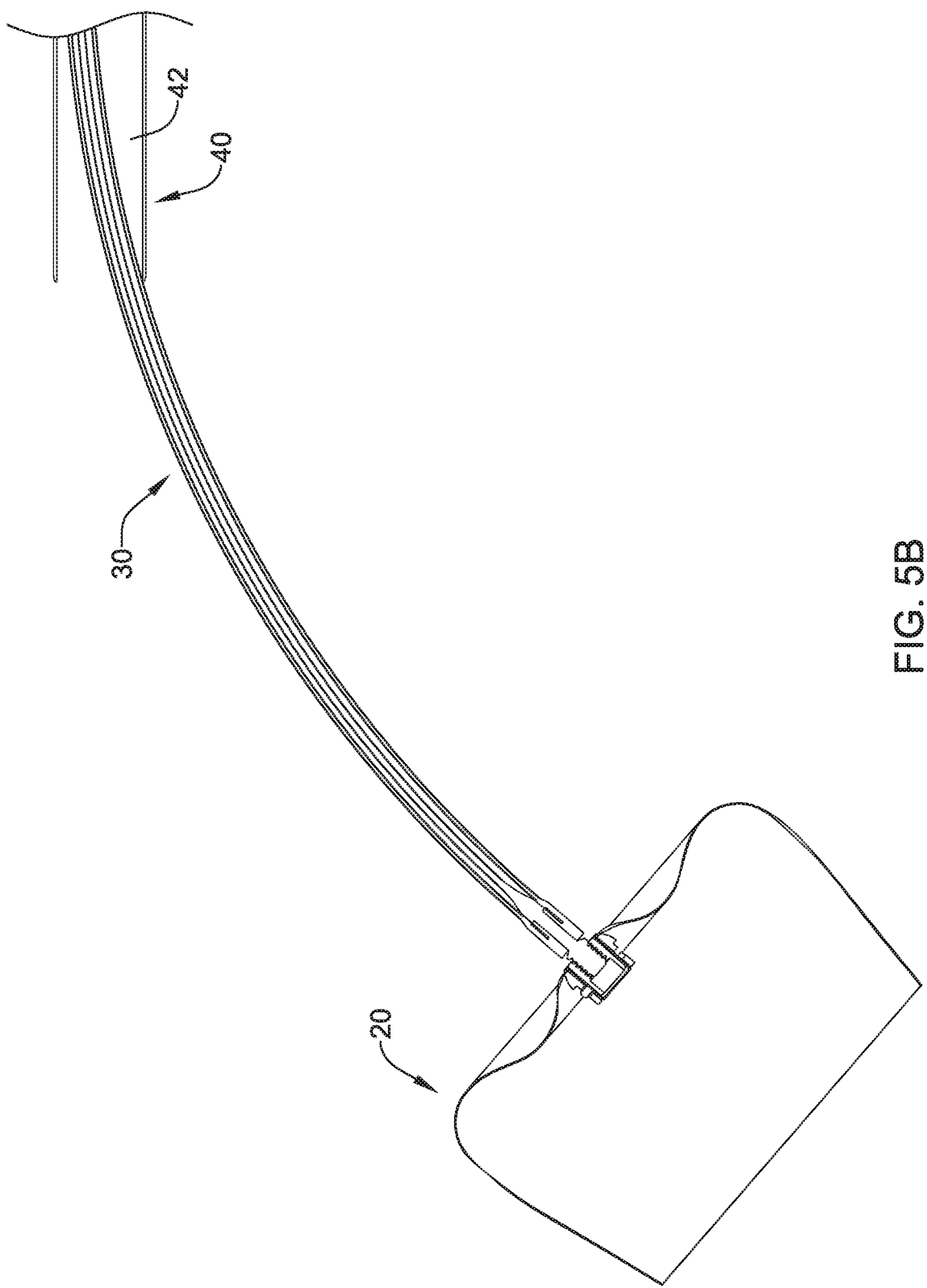

As illustrated in FIGS. 5A and 5B, in some embodiments, a core wire 30 may have a maximum outer diameter that is considerably smaller than a minimum inner diameter of a lumen 42 of a delivery catheter 40. The inner diameter of the lumen 42 of the delivery catheter 40 may be sized to accommodate a medical implant 20 within the lumen 42 in a collapsed configuration. The outer diameter of the core wire 30 may be sized to provide sufficient flexibility to the core wire 30 and the delivery assembly and/or implant system 10 for navigation through a patient's vasculature to a target site (i.e., the left atrial appendage, for example) while maintaining a desired level of torquability and/or pushability.

Figure 6:
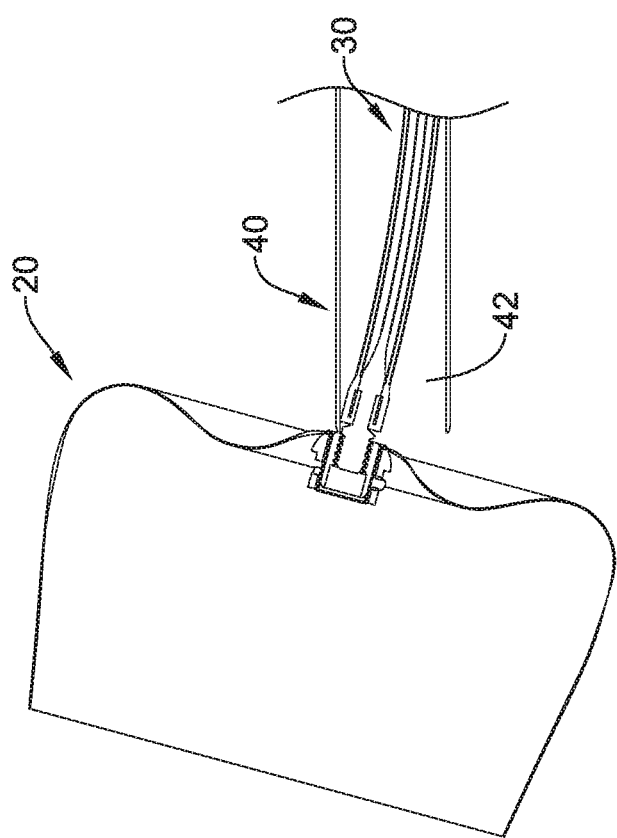
FIG. 6 is a partial cross-sectional view of an example medical implant being retracted into a delivery catheter.

As may be seen in FIGS. 5A and 5B, the difference in size between the core wire 30 and the lumen 42 may allow a significant amount of "play", or lateral movement relative to a central axis of the lumen 42, between the core wire 30 and the delivery catheter 40. As such, a medical implant 20 and/or the distal end 32 of the core wire 30 may become misaligned with the lumen 42 of the delivery catheter 40 after being extended distally from the lumen 42, such as during deployment of the medical implant 20 and/or during removal or recapture of the medical implant 20. During some procedures, it may be necessary to withdraw and/or recapture the medical implant 20 after initial placement, prior to releasing the medical implant 20 from the core wire 30. For example, if an inadequate seal is achieved between the medical implant 20 and the surrounding tissue (i.e., the ostium of the left atrial appendage, for example), a practitioner may recapture the medical implant 20 and deploy it again to ensure proper placement. Alternatively, it may be necessary at some point to remove the medical implant after deployment and release within a patient's anatomy. During recapture procedures, a distal end 44 of the delivery catheter 40 may come into contact with the medical implant 20 and/or the occlusive element disposed thereon, as seen in FIG. 6. If the medical implant 20 is not generally centered within the distal opening of the lumen 42, the forces required to actuate the frame from the expanded configuration to the collapsed configuration may be increased, and in some cases high enough to result in tearing of, or damage to, the occlusive element as the occlusive element is pinched between the frame and the delivery catheter 40, thereby requiring full removal from patient and replacement of the implant 20 before the procedure may proceed. Accordingly, a feature which may result in centering of the implant 20 within the lumen 42 may be beneficial in at least some circumstances.

Figure 7:
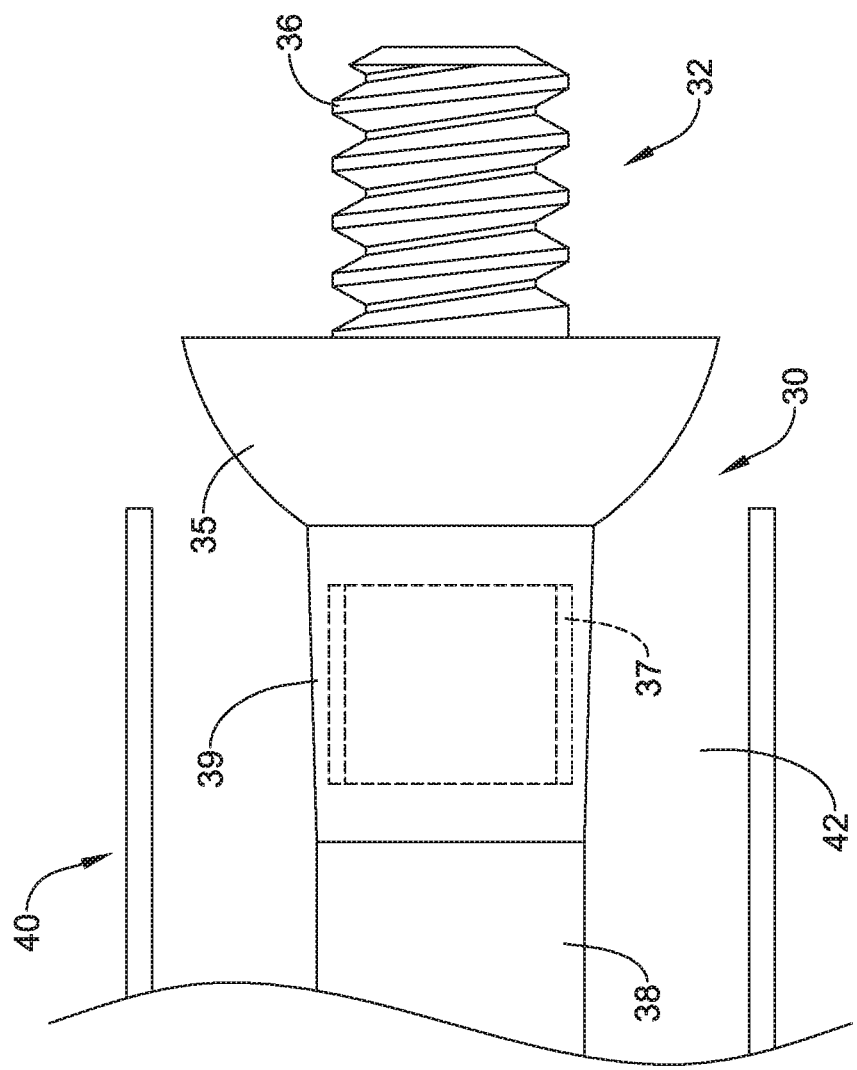
FIG. 7 is a side view of an example guide element.
Figure 8:
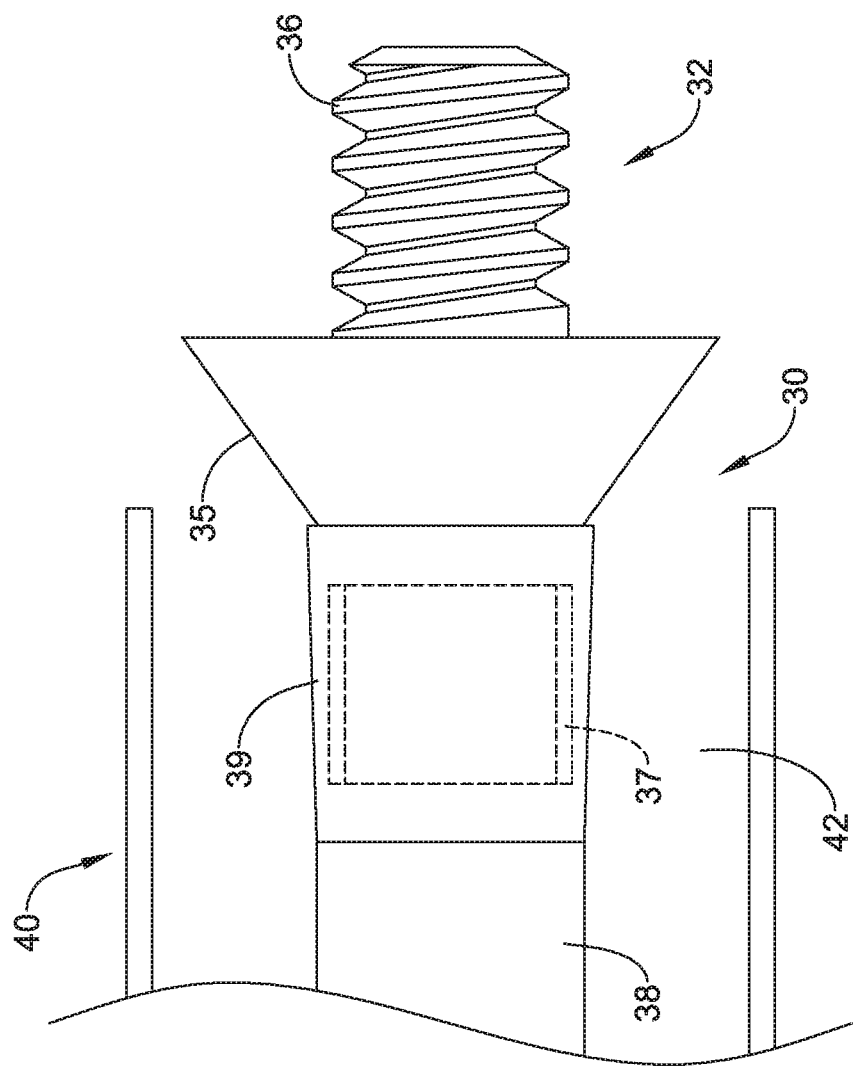
FIG. 8 is a side view of an example guide element.
Figure 9:
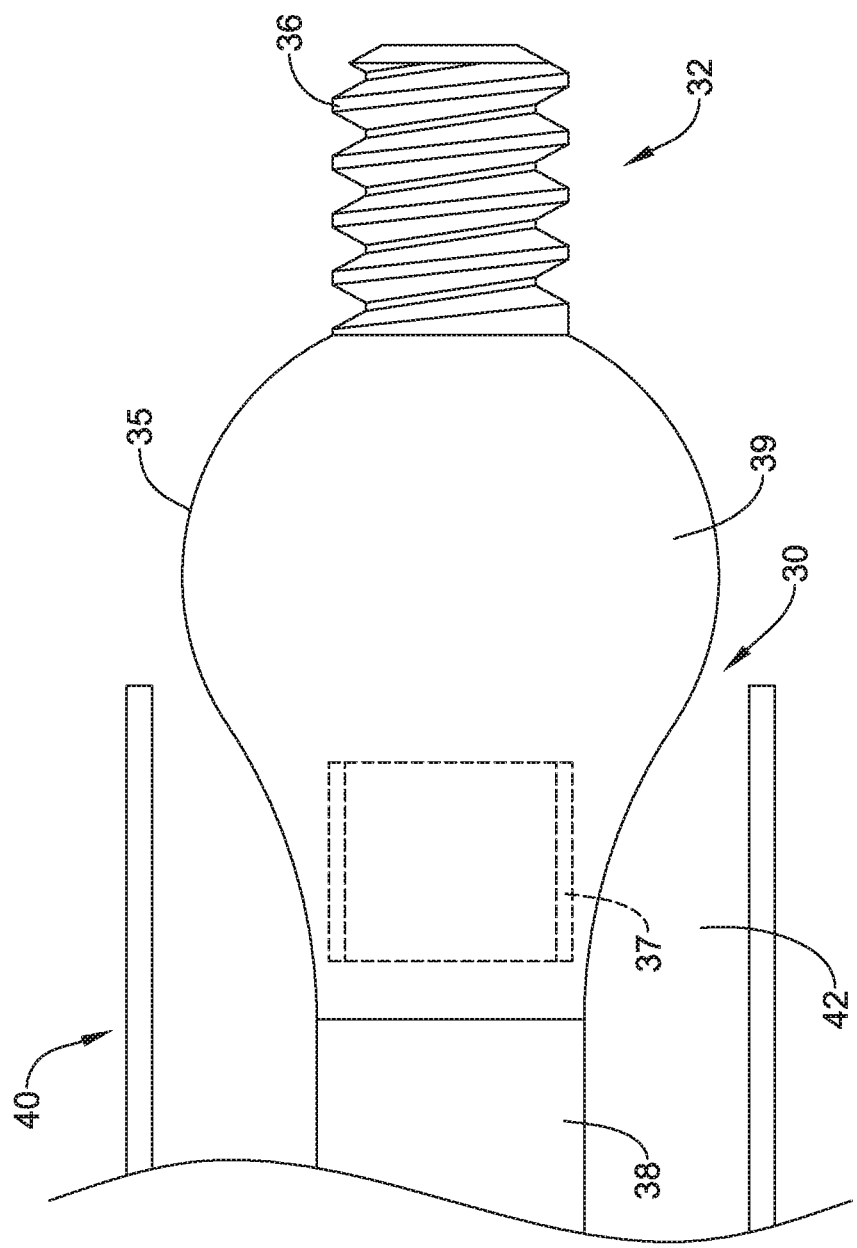
FIG. 9 is a side view of an example guide element.

FIGS. 7-9 illustrate an example core wire 30 having a threaded member 36 at a distal end 32. In some embodiments, the threaded member 36 may be configured and/or adapted to engage, attach to, connect to, and/or mate with a threaded insert of an example medical implant 20. The example core wire 30 may include a guide element 35 disposed about the core wire 30 adjacent a proximal end of the threaded member 36. The guide element 35 may be shaped and/or configured to center the core wire 30 and/or the medical implant 20 within the lumen 42 of the delivery catheter 40. In some embodiments, the guide element 35 may include a curved, convex proximal surface and a generally flat distal surface, as shown in FIG. 7, for example. In some embodiments, the guide element 35 may include a conical proximal surface and a generally flat distal surface, as shown in FIG. 8, for example. In some embodiments, the guide element 35 may include a generally rounded, bulbous, convex outer surface, as shown in FIG. 9, for example. In some embodiments, a distal surface of the guide element 35 may be configured to and/or adapted to contact or engage the medical implant 20 when the threaded member 36 is engaged with, attached to, connected to, and/or mated with the threaded insert, as seen for example in FIGS. 10-11. In some embodiments, a distal surface of the guide element 35 may not contact or engage the medical implant 20 when the threaded member 36 is engaged with, attached to, connected to, and/or mated with the threaded insert, and the distal surface of the guide element 35 may be spaced apart from the medical implant 20.

Figure 10:
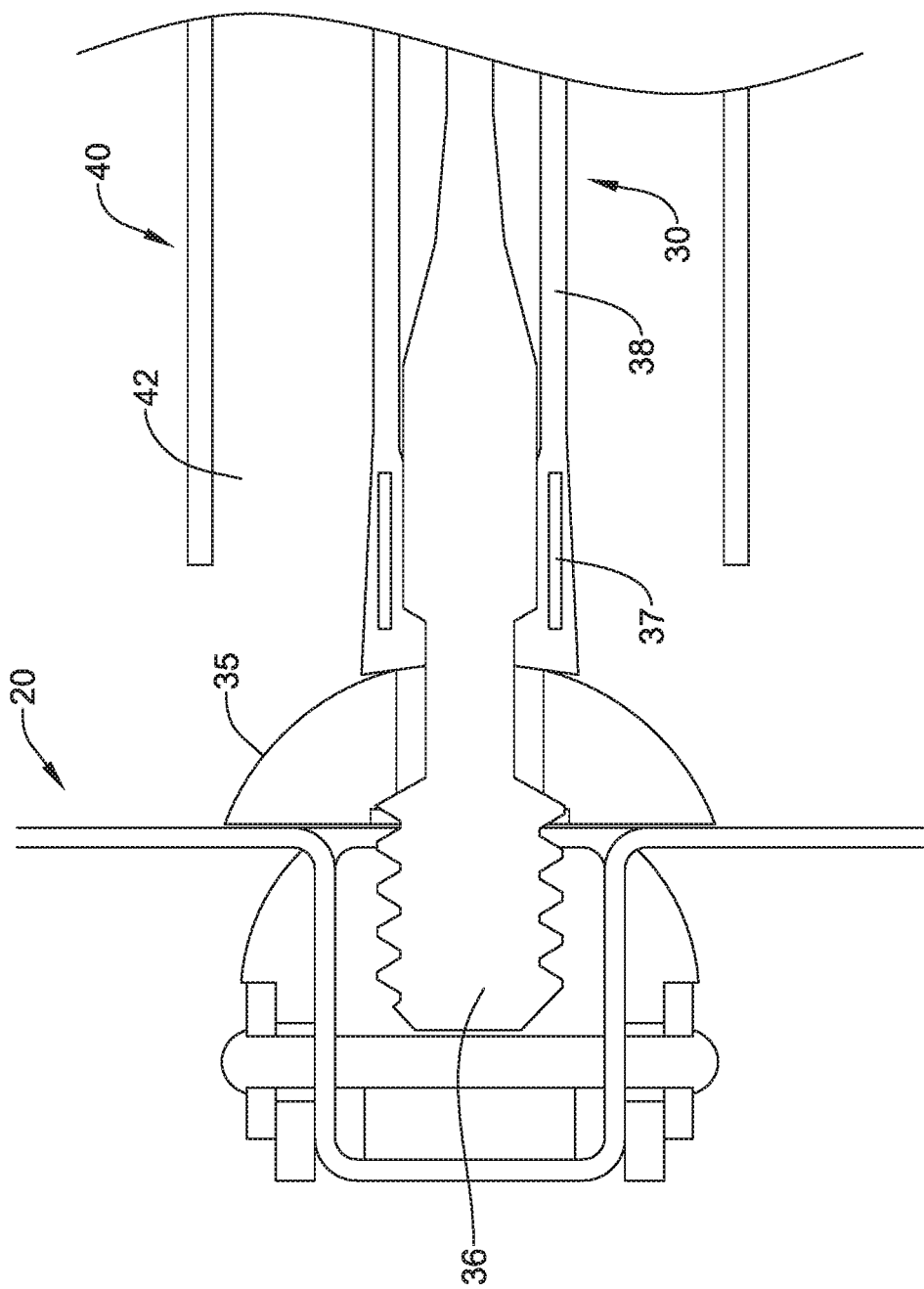
FIG. 10 is a side view of an example medical implant connected to an example core wire having the example guide element of FIG. 7.
Figure 10A:
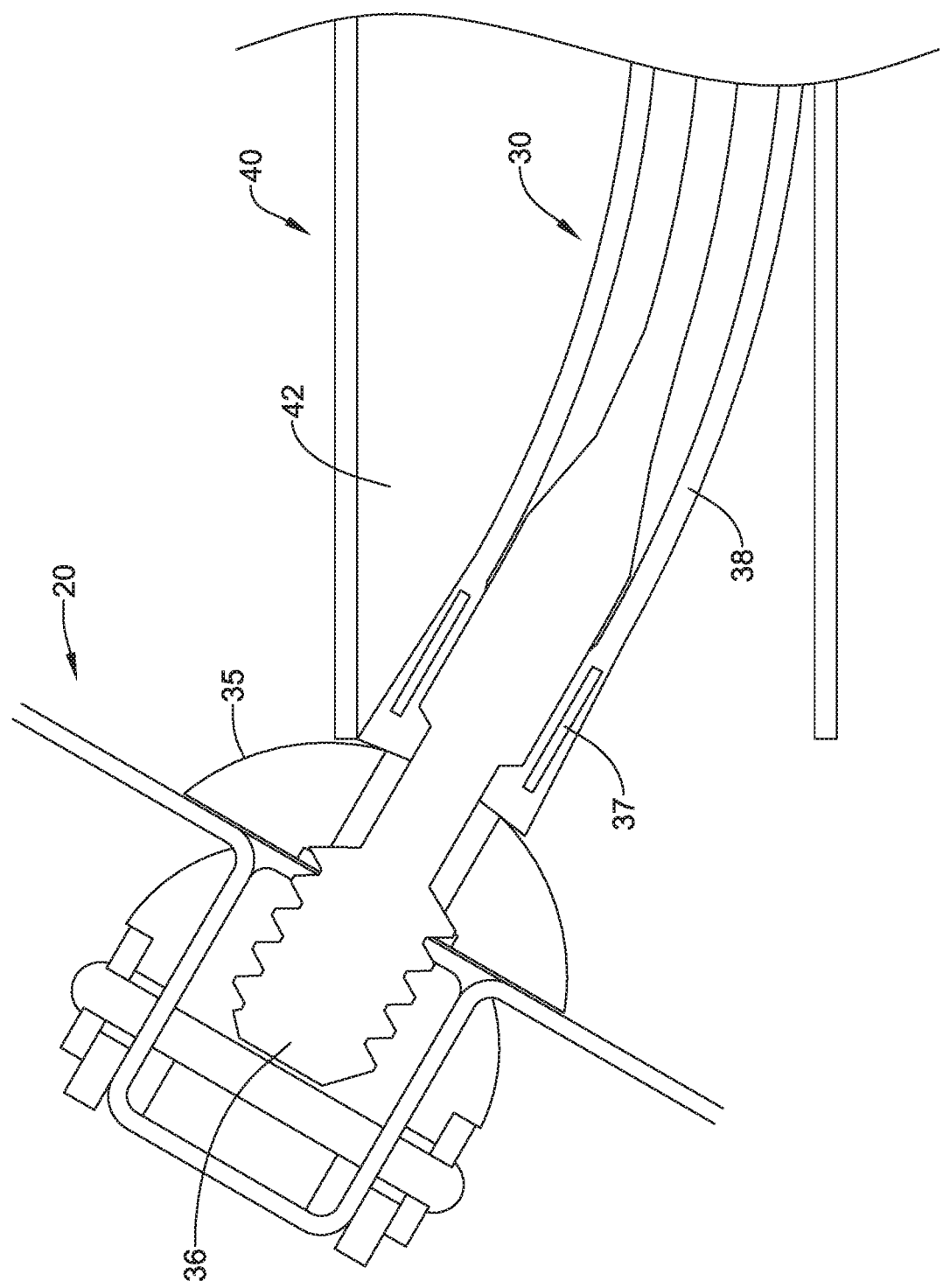
FIG. 10A is a side view of the example medical implant of FIG. 10 misaligned with an example delivery catheter lumen.
Figure 11:
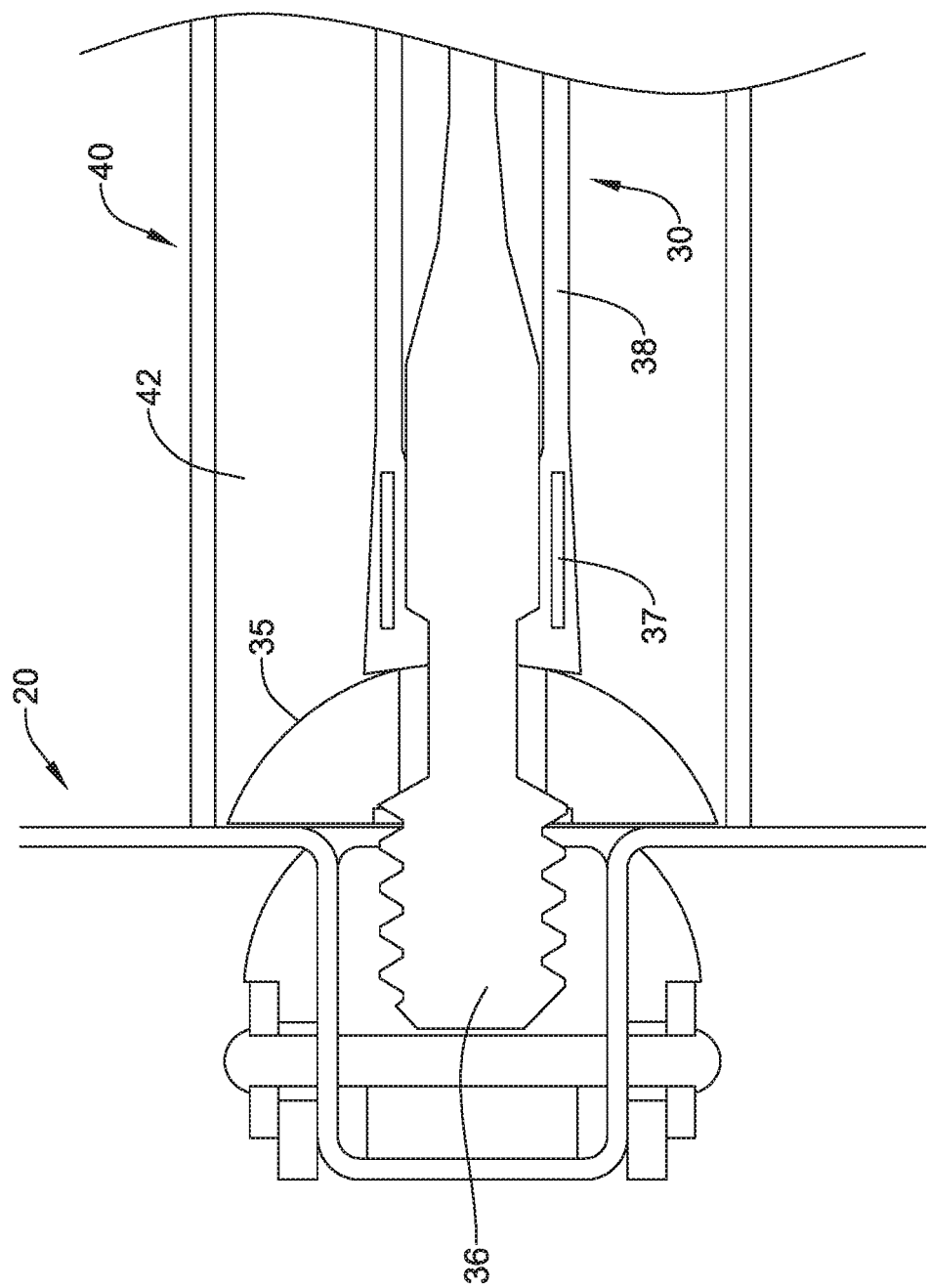
FIG. 11 is a side view of the example medical implant of FIG. 10 being centered with an example delivery catheter lumen.

In some embodiments, an occlusive implant system 10 may include a delivery catheter 40 having a lumen 42 extending therethrough, a core wire 30 slidably and/or rotatably disposed within the lumen 42, the core wire 30 having a threaded member 36 disposed at a distal end 32 thereof, and a medical implant 20 having an expandable frame, an occlusive element disposed on the frame, and a threaded insert coupled to a proximal portion of the frame, wherein the threaded member 36 may be removably coupled to the threaded insert, as shown for example in FIGS. 10-11. In the exemplary figures provided herewith, the example core wire 30 is shown attached to the example medical implant 200 described herein. However, the example core wire 30 may also be used with the example medical implant 100 described herein or other similar medical implants/devices. In some embodiments, the frame may be actuatable between a collapsed configuration and an expanded configuration. In some embodiments, the frame may be self-expanding. In some embodiments, the frame may be manually actuatable from the collapsed configuration to the expanded configuration. In some embodiments, a portion of the occlusive element may be disposed between the threaded insert and the proximal portion of the frame. In some embodiments, a portion of the occlusive element may extend proximally of the threaded insert. In some embodiments, the medical implant 20 may include an annular collar member disposed between the proximal portion of the frame and the threaded insert. In some embodiments, the annular collar member and/or the threaded insert may be removably and/or reversibly coupled to, attached to, connected to, and/or engaged with the proximal portion of the frame by a pin element. In some embodiments, the annular collar member and/or the threaded insert may be fixedly and/or permanently coupled to, attached to, connected to, and/or engaged with the proximal portion of the frame, such as by adhesion, welding, mechanical fastening, and the like.

In some embodiments the core wire 30 may include a guide element 35 disposed adjacent a proximal end of the threaded member 36. In some embodiments, the guide element 35 may be configured and/or adapted to center the core wire 30 within the lumen 42 of the delivery catheter 40. In some embodiments, the guide element 35 may be slidably disposed about the core wire 30. In some embodiments, the guide element 35 may be positioned against the threaded member 36 and axially retained in place by a polymeric jacket 38 disposed over and/or on the core wire 30 and in contact with the guide element 35 at a distal end of the polymeric jacket 38. In some embodiments, the guide element 35 may be fixedly and/or permanently attached to the core wire 30, such as by adhesion, welding, mechanical fastening, and the like. In some embodiments, the guide element 35 may be integrally formed with the core wire 30 as a monolithic unit. In some embodiments, a marker band 37 may be disposed about the core wire 30 adjacent the guide element 35. In some embodiments, the marker band 37 may be disposed over the polymeric jacket 38 and may crimp a distal portion of the polymeric jacket 38 covering the core wire 30 onto the core wire 30. In some embodiments, a discrete piece of polymeric material 39 may be disposed over the marker band 37, as seen for example in FIGS. 7-9. In some embodiments, the discrete piece of material 39 may be heated and/or joined to the polymeric jacket 38, such as by reflow, for example, to form a single polymeric cover member. In some embodiments, the marker band 37 may be at least partially encapsulated by the polymeric jacket 38, the discrete piece of polymeric material 39, and/or the polymeric cover member. In some embodiments, the discrete piece of polymeric material 39 may form the guide element 35, as seen for example in FIG. 9.

In some embodiments, a core wire 30 may include a stepped outer diameter and/or a narrowed distal section adjacent a threaded member 36 disposed at the distal end 32, as may be seen in FIGS. 10-11. A polymeric jacket 38 disposed over and/or on the core wire 30 may be formed, crimped, or otherwise forced into place over the narrowed distal section, resulting in a portion of the polymeric jacket 38 being mechanically locked into place and preventing the polymeric jacket 38 from sliding proximally relative to the core wire 30. In some embodiments, the marker band 37 may mechanically lock the polymeric jacket 38 in place relative to the core wire 30. The mechanical locking may occur with or without the guide element 35 disposed adjacent the threaded member 36.

A method of making a centering core wire may include some or all of the steps of:

obtaining or providing an elongate core wire 30 having a threaded member 36 disposed at a distal end 32 thereof;

obtaining or providing a guide element 35 having an aperture or lumen disposed therein;

inserting a proximal end 34 of the elongate core wire 30 into the aperture of lumen, such that a proximally-facing surface of the guide element 35 provides a generally tapered, angled, or convex surface in a radially outward and distal direction from the core wire 30;

sliding the guide element 35 distally over the elongate core wire 30 and into contact with a proximal end of the threaded member 36;

applying a polymeric jacket 38 over the elongate core wire 30 from the proximal end 34 of the elongate core wire 30 to the guide element 35, wherein the polymeric jacket 38 axially holds and/or retains the guide element 35 against the threaded member 36;

disposing a marker band 37 over the polymeric jacket 38 adjacent the guide element 35;

crimping the marker band 37 onto the elongate core wire 30 such that the polymeric jacket 38 is fixed in position along the elongate core wire 30;

disposing a piece of polymeric material 39 about the marker band 37; and heating the polymeric jacket 38 and the piece of polymeric material 39 such that the polymeric jacket 38 and the piece of polymeric material 39 are joined together by reflow to form a polymeric cover member.

In some embodiments of the method, the marker band 37 may be at least partially encapsulated by reflow of the polymeric jacket 38 and the piece of polymeric material 39. In other words, the marker band 37 may be at least partially encapsulated by the polymeric cover member formed by reflow of the polymeric jacket 38 and the piece of polymeric material 39. In some embodiments of the method, the elongate core wire 30 may include a stepped outer diameter and/or a narrowed section adjacent the threaded member 36 for providing a mechanical interlock between the core wire 30 and the polymeric jacket 38.

FIGS. 3 and 4 illustrate an example medical implant having a membrane or occlusive element disposed over at least a portion of the frame. In some embodiments, at least some of the plurality of proximally-facing hooks project through the membrane or occlusive element. In some embodiments, the membrane or occlusive element may be attached to the frame at each proximally-facing hook, for example, by passing each proximally-facing hook through the membrane or occlusive element, such as through a pore or aperture. In some embodiments, the membrane or occlusive element may be attached to the frame by other suitable attachment means, such as but not limited to, adhesive(s), sutures or thread(s), welding or soldering, or combinations thereof. In some embodiments, the membrane or occlusive element may be permeable or impermeable to blood and/or other fluids, such as water. In some embodiments, the membrane or occlusive element may include a polymeric membrane, a metallic or polymeric mesh, a porous filter-like material, or other suitable construction. In some embodiments, the membrane or occlusive element prevents thrombi (i.e. blood clots, etc.) from passing through the membrane or occlusive element and out of the left atrial appendage into the blood stream. In some embodiments, the membrane or occlusive element promotes endothelization after implantation, thereby effectively removing the left atrial appendage from the patient's circulatory system.

The frame may be compliant and substantially conform to and/or be in sealing engagement with the shape and/or geometry of a lateral wall of a left atrial appendage in the expanded configuration. In some embodiments, the medical implant may expand to a size, extent, or shape less than or different from a maximum unconstrained extent, as determined by the surrounding tissue and/or lateral wall of the left atrial appendage. Reducing the thickness of the plurality of struts may increase the flexibility and compliance of the support frame and/or the implant, thereby permitting the implant to conform to the tissue around it, rather than forcing the tissue to conform to the implant.

In some embodiments, the plurality of struts of the frame, the plurality of proximally-facing hooks, and/or the core wire may be formed of or include a metallic material, a metallic alloy, a ceramic material, a rigid or high performance polymer, a metallic-polymer composite, combinations thereof, and the like. Some examples of some suitable materials may include metallic materials and/or alloys such as stainless steel (e.g., 303, 304v, or 316L stainless steel), nickel-titanium alloy (e.g., nitinol, such as super elastic or linear elastic nitinol), nickel-chromium alloy, nickel-chromium-iron alloy, cobalt alloy, nickel, titanium, platinum, or alternatively, a polymer material, such as a high performance polymer, or other suitable materials, and the like. The word nitinol was coined by a group of researchers at the United States Naval Ordinance Laboratory (NOL) who were the first to observe the shape memory behavior of this material. The word nitinol is an acronym including the chemical symbol for nickel (Ni), the chemical symbol for titanium (Ti), and an acronym identifying the Naval Ordinance Laboratory (NOL).

In some embodiments, the plurality of struts of the frame, the plurality of proximally-facing hooks, and/or the marker band may be mixed with, may be doped with, may be coated with, or may otherwise include a radiopaque material. Radiopaque materials are understood to be materials capable of producing a relatively bright image on a fluoroscopy screen or another imaging technique such as X-ray during a medical procedure. This relatively bright image aids the user of device in determining its location. Suitable radiopaque materials may include, but are not limited to, bismuth subcarbonate, iodine, gold, platinum, palladium, tantalum, tungsten or tungsten alloy, and the like.

In some embodiments, the membrane or occlusive element may be formed of or include a polymeric material, a metallic or metallic alloy material, a metallic-polymer composite, combinations thereof, and the like. In some embodiments, the membrane or occlusive element is preferably formed of polyethylene terephthalate (PET) such as DACRON®, or expanded polytetrafluoroethylene (ePTFE). Other examples of suitable polymers may include polyurethane, a polyether-ester such as ARNITEL® available from DSM Engineering Plastics, a polyester such as HYTREL® available from DuPont, a linear low density polyethylene such as REXELL®, a polyamide such as DURETHAN® available from Bayer or CRISTAMID® available from Elf Atochem, an elastomeric polyamide, a block polyamide/ether, a polyether block amide such as PEBA available under the trade name PEBAX®, silicones, polyethylene, Marlex high-density polyethylene, polytetrafluoroethylene (PTFE), polyetheretherketone (PEEK), polyimide (PI), and polyetherimide (PEI), a liquid crystal polymer (LCP) alone or blended with other materials.

In some embodiments, the delivery catheter and/or the medical implant may be made from, may be mixed with, may be coated with, or may otherwise include a material that provides a smooth, slippery outer surface. In some embodiments, the delivery catheter and/or the medical implant may include or be coated with a lubricious coating, a hydrophilic coating, a hydrophobic coating, a drug-eluting material, an anti-thrombus coating, or other suitable coating depending on the intended use or application.

It should be understood that although the above discussion was focused on a medical device and methods of use within the vascular system of a patient, other embodiments of medical devices or methods in accordance with the disclosure can be adapted and configured for use in other parts of the anatomy of a patient. For example, devices and methods in accordance with the disclosure can be adapted for use in the digestive or gastrointestinal tract, such as in the mouth, throat, small and large intestine, colon, rectum, and the like. For another example, devices and methods can be adapted and configured for use within the respiratory tract, such as in the mouth, nose, throat, bronchial passages, nasal passages, lungs, and the like. Similarly, the apparatus and/or medical devices described herein with respect to percutaneous deployment may be used in other types of surgical procedures as appropriate. For example, in some embodiments, the medical devices may be deployed in a non-percutaneous procedure, such as an open heart procedure. Devices and methods in accordance with the invention can also be adapted and configured for other uses within the anatomy.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed:

1. An occlusive implant system, comprising:
   a catheter having a lumen extending therethrough;
   a core wire slidably and rotatably disposed within the lumen, the core wire having a threaded member disposed at a distal end thereof; and
   a medical implant having an expandable frame, an occlusive element disposed on the expandable frame, and a threaded insert coupled to a proximal portion of the expandable frame;
   wherein the threaded member is removably coupled to the threaded insert,
   wherein a proximalmost extent of the threaded insert is substantially coplanar with a plane defined by three or more proximalmost extents of the expandable frame in an expanded configuration,
   wherein a proximal portion of the occlusive element is substantially coplanar with the proximalmost extent of the threaded insert and the plane defined by the proximalmost extent of the expandable frame in the expanded configuration.

2. The occlusive implant system of claim 1, wherein a portion of the occlusive element is disposed between the threaded insert and the proximal portion of the expandable frame.

3. The occlusive implant system of claim 1, wherein a portion of the occlusive element extends proximally of the threaded insert.

4. The occlusive implant system of claim 1, wherein the core wire includes a guide element disposed adjacent a proximal end of the threaded member, the guide element being configured to center the core wire within the catheter.

5. The occlusive implant system of claim 4, wherein the guide element includes a convex proximal surface and a generally flat distal surface.

6. The occlusive implant system of claim 4, wherein the guide element includes a conical proximal surface and a generally flat distal surface.

7. The occlusive implant system of claim 4, wherein the guide element includes a generally rounded convex outer surface.

8. The occlusive implant system of claim 4, wherein the guide element is disposed about the core wire.

9. The occlusive implant system of claim 8, wherein the guide element is fixedly attached to the core wire.

10. The occlusive implant system of claim 4, wherein the guide element is slidably disposed about the core wire.

11. The occlusive implant system of claim 10, wherein the guide element is positioned against the threaded member and axially retained in place by a polymeric jacket.

* * * * *